US012754314B2

(12) United States Patent
Baker et al.

(10) Patent No.: US 12,754,314 B2
(45) Date of Patent: Oct. 6, 2026

(54) COAXIAL TIME-OF-FLIGHT OPTICAL FIBER DISTANCE MEASUREMENT

(71) Applicant: GYRUS ACMI, INC., Westborough, MA (US)

(72) Inventors: Charles A. Baker, Rogers, MN (US); David Marcus, Northborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 331 days.

(21) Appl. No.: 18/464,573

(22) Filed: Sep. 11, 2023

(65) Prior Publication Data

US 2024/0111048 A1 Apr. 4, 2024

Related U.S. Application Data

(60) Provisional application No. 63/377,889, filed on Sep. 30, 2022.

(51) Int. Cl.
*G01S 17/10* (2020.01)
*A61B 1/05* (2006.01)
(Continued)

(52) U.S. Cl.
CPC ................ *G01S 17/10* (2013.01); *A61B 1/05* (2013.01); *A61B 1/0676* (2013.01); *A61B 18/24* (2013.01);
(Continued)

(58) Field of Classification Search
CPC ...... G01S 7/4865; G01S 17/10; G01S 7/4818; A61B 2018/00505; A61B 2018/00511;
(Continued)

(56) References Cited

U.S. PATENT DOCUMENTS

2011/0306956 A1 12/2011 Islam
2020/0038106 A1 * 2/2020 Pieper .................... A61B 34/30
(Continued)

FOREIGN PATENT DOCUMENTS

CN 113290562 A 8/2021
CN 117796903 4/2024
(Continued)

OTHER PUBLICATIONS

"Japanese Application Serial No. 2023-171260, Examiners Decision of Final Refusal mailed Mar. 11, 2025", W English Translation, 12 pgs.

(Continued)

*Primary Examiner* — Ryan N Henderson
*Assistant Examiner* — Pamela F Wu
(74) *Attorney, Agent, or Firm* — Schwegman Lundberg & Woessner, P.A.

(57) ABSTRACT

In a laser tissue ablation system, a distal end of an optical fiber can extend from an endoscope. The optical fiber can receive therapeutic laser light pulses at first times, receive measurement light pulses at second times, direct the therapeutic laser light pulses and the measurement light pulses toward a target, collect, as collected light pulses, at least some of the measurement light pulses that are reflected from the target, and direct, as return light pulses, at least some of the collected light pulses away from the distal end of the optical fiber. An optical detector can sense at least some of the return light pulses. Processor circuitry can perform a time-of-flight analysis of the sensed return light pulses to determine a spacing between the distal end of the optical fiber and the target and can generate a spacing data signal representing the determined spacing.

20 Claims, 3 Drawing Sheets

(51) Int. Cl.

| | |
|---|---|
| ***A61B 1/06*** | (2006.01) |
| ***A61B 18/24*** | (2006.01) |
| ***G01S 7/481*** | (2006.01) |
| ***G01S 7/4865*** | (2020.01) |
| *A61B 1/00* | (2006.01) |
| *A61B 17/00* | (2006.01) |
| *A61B 18/00* | (2006.01) |

(52) U.S. Cl.
CPC .......... *G01S 7/4818* (2013.01); *G01S 7/4865* (2013.01); *A61B 1/00045* (2013.01); *A61B 2017/00367* (2013.01); *A61B 2018/00577* (2013.01)

(58) Field of Classification Search
CPC ..... A61B 18/26; A61B 2018/263; A61B 1/05; A61B 1/00087; A61B 1/00098; A61B 1/00097; A61B 1/00101; A61B 1/018; A61B 1/00133; A61B 1/012; A61B 1/0008; A61B 1/0669; A61B 1/07; A61B 18/24; A61B 1/0638; A61B 2090/061
USPC ................................ 600/108, 104, 160, 182
See application file for complete search history.

(56) References Cited

U.S. PATENT DOCUMENTS

| | | | | |
|---|---|---|---|---|
| 2020/0288950 | A1* | 9/2020 | Petroff ............... | A61B 17/1214 |
| 2021/0038309 | A1 | 2/2021 | Talbot et al. | |
| 2021/0161364 | A1 | 6/2021 | Fukushima et al. | |
| 2021/0369347 | A1 | 12/2021 | Brown et al. | |
| 2021/0378745 | A1 | 12/2021 | Fukushima et al. | |
| 2023/0314277 | A1 | 10/2023 | Waisman et al. | |
| 2024/0016543 | A1* | 1/2024 | Altshuler ............... | A61B 18/22 |
| 2024/0264307 | A1* | 8/2024 | Nakada ................... | G01S 17/32 |

FOREIGN PATENT DOCUMENTS

| | | |
|---|---|---|
| DE | 102023126770 | 4/2024 |
| JP | 2008104791 | 5/2008 |
| JP | 2016520334 | 7/2016 |
| JP | 7764445 B2 | 10/2025 |
| WO | 2014133476 | 9/2014 |
| WO | 2020021590 | 1/2020 |
| WO | 2020174686 | 9/2020 |
| WO | 2021026161 | 2/2021 |
| WO | 2022032211 | 2/2022 |
| WO | 2022198638 | 9/2022 |

OTHER PUBLICATIONS

"Japanese Application Serial No. 2023-171260, Response filed May 29, 2025 to Examiners Decision of Final Refusal mailed Mar. 11, 2025", w english claims, 18 pgs.
"Japanese Application Serial No. 2023-171260, Notification of Reasons for Refusal mailed Sep. 30, 2024", W English Translation, 16 pgs.
"Japanese Application Serial No. 2023-171260, Response filed Nov. 12, 2024 to Notification of Reasons for Refusal mailed Sep. 30, 2024", w current English claims, 17 pgs.
"Indian Application Serial No. 202344065906, First Examination Report mailed Jul. 21, 2025", 6 pgs.
"Indian Application Serial No. 202344065906, Response filed Jan. 12, 2026 to First Examination Report mailed Jul. 21, 2025", w claims, 27 pgs.
"Indian Application Serial No. 202344065906, Hearing Notice mailed May 13, 2026", 2 pgs.

* cited by examiner

COAXIAL TIME-OF-FLIGHT OPTICAL FIBER DISTANCE MEASUREMENT

CROSS-REFERENCE TO RELATED APPLICATION

This application claims the benefit of U.S. Provisional Application No. 63/377,889, filed Sep. 30, 2022, which is hereby incorporated by reference in its entirety.

FIELD OF THE DISCLOSURE

This document relates generally to endoscopic systems, and more specifically relates to systems and methods for determining and controlling a distance between an endoscope tip and a target.

BACKGROUND OF THE DISCLOSURE

An operator, such as a physician, practitioner, or user, can use an endoscope to provide visual access to an internal location of a patient. The operator can insert an endoscope into a patient's body. The endoscope can deliver light to a target being examined, such as a target anatomy or object. The endoscope can collect light that is reflected from the object. The reflected light can carry information about the target being examined.

An endoscope can include a working channel. In some examples, the operator can perform suction through the working channel. In some examples, the operator can pass instruments, such as brushes, biopsy needles or forceps, through the working channel. In some examples, the operator can perform minimally invasive surgery through the working channel, such as to remove unwanted tissue or foreign objects from the body of the patient.

An endoscope can use a laser or plasma system to perform laser therapy, such as ablation, coagulation, vaporization, fragmentation, lithotripsy, and others. In laser therapy, the operator can use the endoscope to deliver surgical laser energy to various target treatment areas, such as soft or hard tissue. In lithotripsy, the operator can use the endoscope to deliver surgical laser energy to break down calculi structures in the patient's kidney, gallbladder, ureter, or other stone-forming regions, or to ablate large calculi into smaller fragments.

SUMMARY

In an example, a laser tissue ablation system can comprise: an endoscope; an optical fiber including a distal end extending from the endoscope, the optical fiber configured to: receive therapeutic laser light pulses at first times; receive measurement light pulses at second times different from the first times; direct the therapeutic laser light pulses and the measurement light pulses along the optical fiber to emerge from the distal end of the optical fiber toward a target; collect, as collected light pulses, at least some of the measurement light pulses that are reflected from the target; and direct, as return light pulses, at least some of the collected light pulses along the optical fiber away from the distal end of the optical fiber; an optical detector configured to sense at least some of the return light pulses; and processor circuitry configured to: perform a time-of-flight analysis of the sensed return light pulses to determine a spacing between the distal end of the optical fiber and the target; and generate a spacing data signal representing the determined spacing.

In an example, a method for operating a laser tissue ablation system that includes an endoscope and an optical fiber including a distal end extending from the endoscope can comprise: receiving, with the optical fiber, therapeutic laser light pulses at first times; receiving, with the optical fiber, measurement light pulses at second times different from the first times; directing the therapeutic laser light pulses and the measurement light pulses along the optical fiber to emerge from the distal end of the optical fiber toward a target; collecting, with the optical fiber, as collected light pulses, at least some of the measurement light pulses that are reflected from the target; directing, as return light pulses, at least some of the collected light pulses along the optical fiber away from the distal end of the optical fiber; sensing, with an optical detector, at least some of the return light pulses; performing a time-of-flight analysis of the sensed return light pulses to determine a spacing between the distal end of the optical fiber and the target; and generating a spacing data signal representing the determined spacing.

In an example, a laser tissue ablation system can comprise: a therapeutic laser light source configured to generate therapeutic laser light pulses at first times; a measurement light source configured to generate measurement light pulses at second times different from the first times; an endoscope spaced apart from the therapeutic laser light source and the measurement light source; an optical fiber including a distal end extending from the endoscope and configured to: direct the therapeutic laser light pulses and the measurement light pulses along the optical fiber to emerge from the distal end of the optical fiber toward a target; collect, as collected light pulses, at least some of the measurement light pulses that are reflected from the target; direct, as return light pulses, at least some of the collected light pulses along the optical fiber away from the distal end of the optical fiber; collect, as collected therapeutic light pulses, at least some of the therapeutic light pulses that are reflected from the target; and direct, as return therapeutic light pulses, at least some of the collected therapeutic light pulses along the optical fiber away from the distal end of the optical fiber; an optical detector configured to sense at least some of the return light pulses; a spectrometer configured to analyze the return therapeutic light pulses; processor circuitry configured to: perform a time-of-flight analysis of the sensed return light pulses to determine a spacing between the distal end of the optical fiber and the target; generate a spacing data signal representing the determined spacing; and electronically communicate the spacing data signal to the spectrometer; an illumination light source disposed at a distal end of the endoscope and configured to illuminate the target with visible illumination light; a camera disposed at the distal end of the endoscope and configured to generate a video image of the illuminated target; and a display coupled to the processor circuitry and configured to display the video image of the illuminated target and a visual representation of the determined spacing represented by the spacing data signal.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

In a laser therapy treatment, a practitioner can position a distal end of an endoscope close to a target, such as a kidney stone. The endoscope can include an optical fiber that can deliver therapeutic laser light to the target, such as via a distal end of the optical fiber. During the treatment, it can be beneficial to dynamically monitor or dynamically control a separation between the distal end of the optical fiber and the target. For example, if the distal end of the optical fiber is positioned too close to the target, it could lead to a condition known as flashing, which can degrade the distal end of the optical fiber. Likewise, if the distal end of the optical fiber is positioned too far from the target, then a significant fraction of the therapeutic laser light can be absorbed before reaching the target, which can decrease an efficiency of the laser therapy treatment or cause the treatment to take longer.

The laser tissue ablation system described in detail below can use time-of-flight techniques on light that returns through the optical fiber to dynamically monitor the separation between the distal end of the optical fiber and the target (referred to as "real-time separation" in the following paragraphs).

Specifically, during a laser therapy treatment, the surgical system can use time-of-flight techniques on light that returns through the optical fiber to dynamically determine the real-time separation, and, in response to the real-time separation value, can provide user feedback and/or take an action. For example, the surgical system can provide user feedback representing the real-time separation to the practitioner, such as displaying a numerical value on a display, displaying a graphical representation of the real-time separation on a display, displaying visual indicators that show when the real-time separation is in one of several specified ranges (such as too small, acceptable, too large, and so forth), playing an audio alert, and others. As another example, the surgical system can take an action in response to the real-time separation, such as distally retracting the optical fiber if the real-time separation is too low, automatically positioning the distal end of the optical fiber to have a specified value of real-time separation, or others.

Because the time-of-flight measurement uses light that returns through the optical fiber, the measurement technique can be referred to as being coaxial.

Figure 1:
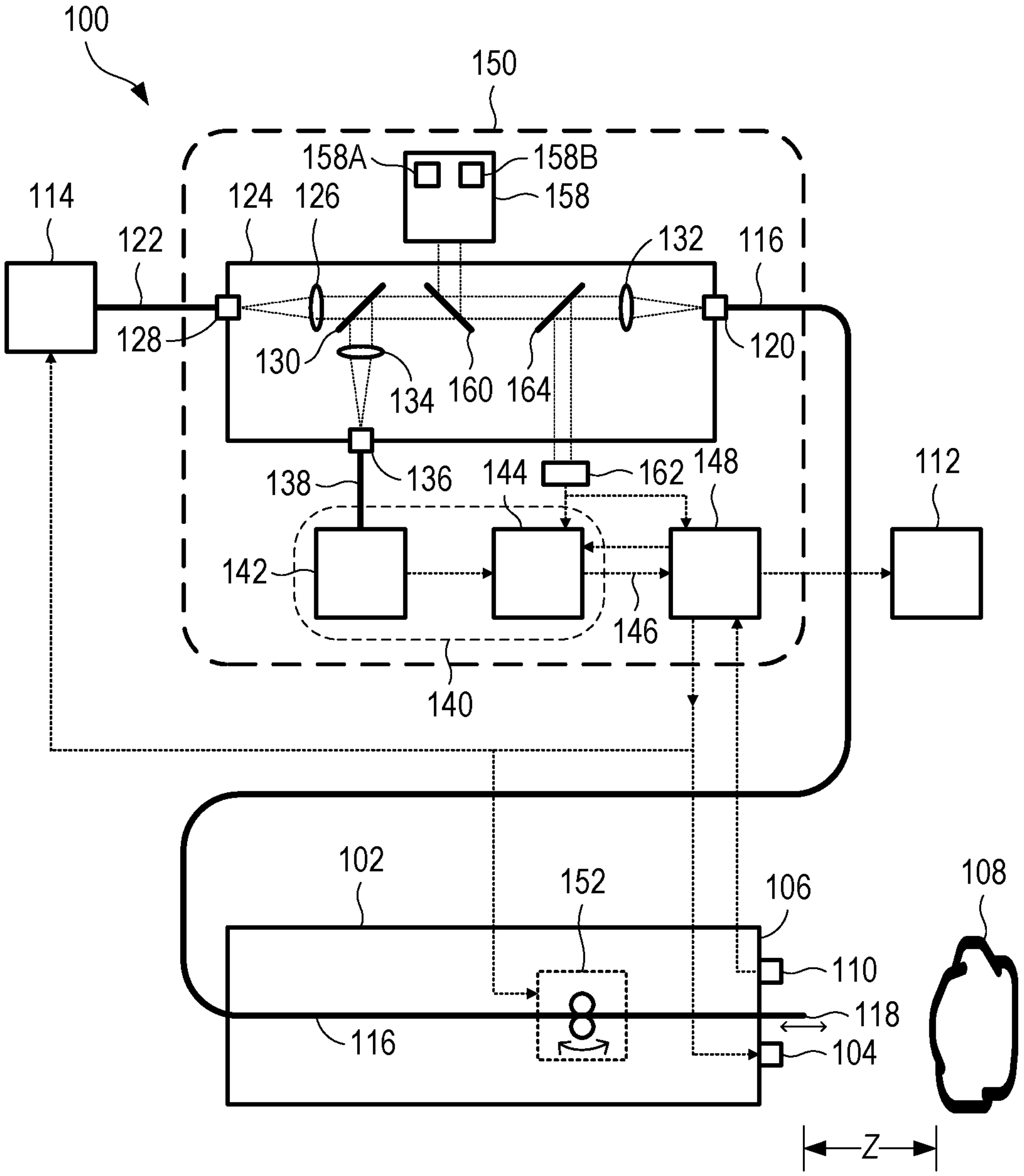
FIG. 1 shows a side-view schematic drawing of an example of a laser tissue ablation system.

FIG. 1 shows a side-view schematic drawing of an example of a laser tissue ablation system 100. The laser tissue ablation system 100 can include an endoscope 102. The endoscope 102 can be grippable by the operator, who can position the endoscope 102 as needed to view and ablate one or more targets, such as kidney stones, in one or more internal locations of the patient. In some examples, the endoscope 102 can be rigid. In one or more examples, the endoscope 102 can be elongated along an elongation axis. The endoscope 102 can include one or more channels, passages, or apertures that extend through the endoscope 102 along the elongated axis. For example, the endoscope 102 can include a working channel. In some examples, the operator can perform suction through the working channel. In some examples, the operator can pass instruments, such as brushes, biopsy needles or forceps, through the working channel. In some examples, the operator can perform minimally invasive surgery through the working channel, such as to remove unwanted tissue or foreign objects from the body of the patient. As another example, the endoscope 102 can include an irrigation channel, which can supply irrigant to the target site, such as to flush away pieces of the target. Other channels can also be used.

The laser tissue ablation system 100 can include an illumination light source 104 disposed on a distal end 106 of the endoscope 102. For example, the illumination light source 104 can include one or more light emitting diodes disposed on the distal end 106 of the endoscope 102. In some examples, the light emitting diodes can be white light emitting diodes. For example, a white light emitting diode can include a blue or a violet light emitting diode, coupled with a phosphor that can absorb some or all of the blue or violet light, and in response, can emit light with one or more longer wavelengths, such as in the yellow portion of the electromagnetic spectrum. Other illumination light sources can also be used. The illumination light source 104 can illuminate a target 108 with visible light illumination having a visible light illumination spectral range. In some examples, the visible light illumination spectral range can include wavelengths in the visible portion of the electromagnetic spectrum.

The laser tissue ablation system 100 can include a video camera 110 disposed on the distal end 106 of the endoscope 102. In some examples, the video camera 110 can include a lens, a sensor element located at a focal plane of the lens, and electronics that can convert an electrical signal produced by the sensor element into a digital signal. The video camera elements can be located in a relatively small, sealed package at the distal end 106 of the endoscope 102. The video camera 110 can capture a real-time video image of the illuminated target 108.

The laser tissue ablation system 100 can include a video display 112 that can display the video image of the illuminated target 108. For example, the video display 112 can be mounted on or in a rack of equipment, away from the endoscope 102. The video display 112 can provide a real time image of the target 108, illuminated with white light from the illumination light source 104, to the practitioner.

The laser tissue ablation system 100 can include a therapeutic laser light source 114 that can generate laser light, such as in pulsed laser light. In some examples, the therapeutic laser light source 114 can generate therapeutic laser light pulses at first times. The therapeutic laser light source 114 can be located away from the endoscope 102, such that the endoscope 102 can be positionable by the operator, while the therapeutic laser light source 114 can be disposed in a laser housing that can remain in a fixed position, spaced apart from the endoscope 102, during a procedure. In some examples, the therapeutic laser light source 114 can include a thulium fiber laser, which can produce light having one or more wavelengths between about 1920 nm and about 1960 nm. In some examples, the therapeutic laser light source 114 can include a thulium:YAG (yttrium aluminum garnet) laser, which can produce light at a wavelength of 2010 nm. In some examples, the therapeutic laser light source 114 can include a holmium:YAG laser, which can produce light at a wavelength of 2120 nm. In some examples, the therapeutic laser light source 114 can include an erbium:YAG laser, which can produce light at a wavelength of 2940 nm. In some examples, the laser light produced by the therapeutic laser light source 114 can include a first wavelength, such as a wavelength between about 1908 nm and about 2940 nm, or between about 1920 nm and 1960 nm, between about 1900 nm and about 1940 nm, greater than about 1900 nm, greater than about 1800 nm, or others. For these (and other) therapeutic laser light sources, the laser light can have a wavelength or wavelengths in a portion of the electromagnetic spectrum at which water (a major component of tissue) has a relatively high absorption. During a procedure, the tissue can absorb the laser light, can heat locally to a relatively high temperature, and can break apart due to local thermal strains within the tissue.

The laser tissue ablation system 100 can include a measurement light source 158 that can generate measurement light pulses at second times different from the first times. For example, the first and second times can alternate, such that the therapeutic laser light source 114 generates therapeutic laser light pulses at times when the measurement light source 158 is not generating light, and the measurement light source 158 generates measurement light pulses at times when the therapeutic laser light source 114 is not generating light. As another example, the therapeutic laser light source 114 can generate a series of pulses (such as ten pulses), the measurement light source 158 can generate a measurement light pulse, and the sequence of eleven pulses can repeat as needed. These are but examples of schemes for generating measurement light pulses at second times different from the first times; other schemes can also be used.

The laser tissue ablation system 100 can include an optical fiber 116 that can extend from the endoscope 102. In some examples, the optical fiber 116 can be a multi-mode optical fiber. In some examples, the optical fiber 116 can have a distal end 118 that extends from a distal end 106 of the endoscope 102.

The therapeutic laser light source 114 and the measurement light source 158 can direct the therapeutic laser light pulses and the measurement light pulses, respectively, and at different times, into a proximal portion 120 of the optical fiber 116, such as via a therapeutic laser light source optical fiber 122 and a free-space optical coupler/splitter 124. The free-space optical coupler/splitter 124 can include a collimating lens 126 with a focal plane located at a distal end 128 of the therapeutic laser light source optical fiber 122, which can collimate (or at least partially focus) light from the therapeutic laser light source 114. The collimated light can pass through a return-path beamsplitter 130 and be focused by a bi-directional focusing lens 132 onto the proximal portion 120 of the optical fiber 116. The free-space optical coupler/splitter 124 can include an incident-path beamsplitter 160 that can receive the measurement light pulses from the measurement light source 158 and direct the measurement light pulses onto a common optical path with the therapeutic laser light pulses from the therapeutic laser light source 114. In some examples, the therapeutic laser light source 114 can direct the therapeutic laser light pulses along a first optical path, the measurement light source 158 can direct the measurement light pulses along a second optical path, the measurement light pulses being spectrally separated from the therapeutic laser light pulses, and the incident-path beamsplitter 160 can be a dichroic beamsplitter positioned to combine the first and second optical paths to align along a third optical path that extends into the optical fiber 116. The bi-directional focusing lens 132 can direct the therapeutic laser light pulses (for example, at first times) and the measurement light pulses (for example, at second times) onto the proximal portion 120 of the optical fiber 116. The bi-directional focusing lens 132 can collimate the return light that returns through the optical fiber 116. The return-path beamsplitter 130 can direct all or a portion (or a spectral portion) of the return light onto a return-path focusing lens 134, which can focus the return light onto an end 136 of a return-path optical fiber 138. The return-path optical fiber 138 can direct the return light to a sensor (described below). The free-space optical coupler/splitter 124 is but one configuration for such a coupler/splitter. Alternatively, a fiber-based optical coupler/splitter can also be used.

The optical fiber 116 can receive therapeutic laser light pulses at first times. The optical fiber 116 can receive measurement light pulses at second times different from the first times. The optical fiber 116 can direct the therapeutic laser light pulses and the measurement light pulses along the optical fiber 116 to emerge from the distal end 118 of the optical fiber 116 toward the target 108. The optical fiber 116 can collect, as collected light pulses, at least some of the measurement light pulses that are reflected from the target 108. The optical fiber 116 can direct, as return light pulses, at least some of the collected light pulses along the optical fiber 116 away from the distal end 118 of the optical fiber 116.

The laser tissue ablation system 100 can include an optical detector 140 that can sense at least some of the return light pulses. The optical detector 140 can include a light-sensitive sensor element 142, which can convert an optical signal, such as the return light pulses, into an internal electrical signal. The optical detector 140, as shown in the configuration of FIG. 1, can also include sensor circuitry 144, which can convert or process the internal electrical signal from the light-sensitive sensor element 142 into an analog or digital sensor data signal 146 that can be interpreted by the processor circuitry 148 (described below). The optical detector 140 can further include one or more wavelength-sensitive elements, which can allow the sensor circuitry 144 to provide intensity measurements of the return light, as a function of wavelength.

For example, the wavelength-sensitive element of the optical detector 140 can include a dichroic beamsplitter (e.g., implemented as a thin-film coating on the return-path beamsplitter 130) that can separate the measurement light from the therapeutic laser light. The dichroic beamsplitter can have a threshold wavelength, can direct light with wavelengths less than the threshold wavelength along a first optical path, and can direct light with wavelengths greater than the threshold wavelength along a second optical path. The threshold wavelength can have any suitable wavelength value between a wavelength of the measurement light and a wavelength of the therapeutic laser light. In some examples, the dichroic beamsplitter can be implemented as a thin-film coating on a surface of a transparent optical element, such as a prism.

In some configurations, the optical detector 140 can include a dichroic beamsplitter (e.g., implemented as a thin-film coating on the return-path beamsplitter 130) that can receive the return light, direct the therapeutic laser light along a first optical path, and direct the measurement light along a second optical path. The light-sensitive sensor element 142 of the optical detector 140 can include a sensor element or detector that can detect light from the second optical path. In some examples, the light-sensitive sensor element 142 can include a single detector element. In other examples, the light-sensitive sensor element 142 can include a multi-pixel detector element. The optical detector 140 can further include sensor circuitry 144, which can produce one or more sensor data signals 146 in response to light received by the light sensor. The processor circuitry 148 (described below) can analyze the one or more sensor data signals 146 to determine if and/or when a flashing event has occurred.

In some configurations, the sensor circuitry 144 of the optical detector 140 (and, optionally, the wavelength-sensitive element of the optical detector 140) can include a spectrometer that can spectrally measure the return light. For these configurations, the light-sensitive sensor element 142 can include a spectrometer sensor or spectrometer detector, which can receive all or a portion of the return light. For these configurations, the sensor data signal 146 can be a spectrometer output signal that includes data that represents light intensity (or amplitude, or other suitable photometric quantity) as a function of wavelength. The processor circuitry 148 (described below) can analyze the spectrometer output signal to determine a spectral profile of the target 108 and/or a material composition of the target 108.

For configurations in which the optical detector 140 includes a spectrometer, the laser tissue ablation system 100 can optionally perform analysis of the target 108, based on the return light. For example, optical fiber 116 can collect, as collected therapeutic light pulses, at least some of the therapeutic light pulses that are reflected from the target 108. The optical fiber 116 can direct, as return therapeutic light pulses, at least some of the collected therapeutic light pulses along the optical fiber 116 away from the distal end 118 of the optical fiber 116. The spectrometer can analyze the return therapeutic light pulses. In some examples, the processor circuitry 148 (described below) can use the spectral profile of the target 108 to determine a material composition of the target 108, such as by matching the measured spectral profile of the target 108 to one or more of a specified (finite) plurality of predetermined spectral profiles that correspond to known materials. These are but examples; other suitable analyses of the target 108 can also be performed.

The laser tissue ablation system 100 can include processor circuitry 148. In some examples, the processor circuitry 148 may be referred to as a controller. In some examples, the processor circuitry 148 may be implemented purely in software. In some examples, the processor circuitry 148 may be implemented purely in hardware. In some examples, the processor circuitry 148 may be implemented as a combination of software and hardware. In some examples, the processor circuitry 148 may be implemented on a single processor. In some examples, the processor circuitry 148 may be implemented on multiple processors. In some examples, the multiple processors may be housed in a common housing. In some examples, at least two of the multiple processors may be spaced apart in different housings.

In some examples, the free-space optical coupler/splitter 124, the optical detector 140, and the processing circuitry 148 can be included in a housing 150. The therapeutic laser light source 114 can direct laser light into the housing via the therapeutic laser light source optical fiber 122. The optical fiber 116 can direct the laser light from the housing 150 to the endoscope 102 and can tether the endoscope 102 to the housing 150. The video display 112 can optionally be attached to the housing 150 or made integral with the housing 150.

The processor circuitry 148 can perform a time-of-flight analysis of the sensed return light pulses to determine a spacing (Z) (e.g. a real-time separation) between the distal end 118 of the optical fiber 116 and the target 108. The processor circuitry 148 can use one or more measurement techniques to determine the spacing (Z), several examples of which are described presently.

In some examples, the processor circuitry 148 can perform the time-of-flight analysis of the sensed return light pulses by, for an individual return light pulse, determining a time duration between the sensing of the return light pulse by the optical detector and an arrival of a corresponding reference signal. In other words, the processor circuitry 148 can determine the spacing (Z) by directly sensing an arrival time of a particular pulse. Three examples of direct sensing techniques follow.

In a first example, the distal end 118 of the optical fiber 116 can produce a reflection, which can form the reference signal. The measurement light pulses can reflect from the distal end 118 of the optical fiber 116 to form reference light pulses that propagate along the optical fiber 116 away from the distal end 118 of the optical fiber 116. A time duration between the arrival of the reference signal (reflected from the distal end 118 of the optical fiber 116) and the return light pulse (reflected from the target 108) represents a round-trip time of return light pulse as in propagates from the from the distal end 118 of the optical fiber 116 to the target 108, and back. The physical separation can be calculated as one-half the round-trip time duration, multiplied by the speed of light in a vacuum, divided by a refractive index of the medium between the optical fiber 116 and the target 108 (which can be approximated as water).

In a second example, the measurement light source 158 can generate reference electrical pulses at times that correspond to the measurement light pulses, such that the reference electrical pulses can directly form the reference signals (e.g., rather than a signal arising from detection of a pulse).

In a third example, the measurement light source 158 can include a first light source 158A that can generate first measurement light pulses at a first wavelength and a second light source 158B that can generate second measurement light pulses at a second wavelength different from the first wavelength. The optical fiber 116 can include a fiber material having non-zero dispersion such that the first measurement light pulses and the second measurement light pulses propagate along the optical fiber 116 at different speeds, each given by the speed of light in a vacuum divided by the respective refractive index of the fiber material at the respective wavelength. The first measurement light pulses can form the return light pulses. The second measurement light pulses can be sensed by the optical detector 140 to form the corresponding reference signals.

These are but three examples of measurement techniques to determine the spacing (Z) by directly sensing an arrival time of a particular pulse. Other direct sensing techniques can also be used.

Alternatively, the processor circuitry 148 can perform the time-of-flight analysis of the sensed return light pulses without directly sensing an arrival time of a particular pulse. For example, in an example of such an indirect measurement technique, the processor circuitry 148 can perform the time-of-flight analysis of the sensed return light pulses by, for an individual return light pulse: determining a first amount of accumulated light for a first time duration of the return light pulse, determining a second amount of accumulated light for a second time duration of the return light pulse, and using a ratio of the first and second amounts of accumulated light to determine the spacing between the distal end of the optical fiber and the target. Further details regarding indirect measurement techniques are provided in U.S. Patent Application Publication No. US 2021/0161364, which is hereby incorporated by reference in its entirety.

In some examples, the measurement light source 158 can be a LIDAR (Light Detection and Ranging) light source. In some examples, the optical detector 140 can include a LIDAR detector 162. In some examples, the laser tissue ablation system can further include a beamsplitter 164 that can: separate the return light pulses from the return therapeutic light pulses, direct the return light pulses to the LIDAR detector 162, and direct the return therapeutic light pulses to the spectrometer (such as in the sensor circuitry 144). In some examples, the processor circuitry 148 can electronically communicate to the spectrometer (such as in the sensor circuitry 144) data representing the determined spacing (Z).

The processor circuitry 148 can take one or more actions in response to determining the spacing (Z) (e.g. the real-time separation) between the distal end 118 of the optical fiber 116 and the target 108. Several examples of such actions follow.

In a first example, the processor circuitry 148 can generate a spacing data signal representing the determined spacing (Z). In some examples, the spacing data signal can be a digital signal. For example, the spacing data signal can include a variable, stored in memory. The variable can have a value that corresponds to the determined spacing (Z). In some examples, the spacing data signal can be an analog signal. For example, the spacing data signal can include an electrical signal having a voltage value that corresponds to the determined spacing (Z). Other spacing data signals can also be used. The processor circuitry 148 can optionally send the spacing data signal, or data that corresponds to the spacing data signal, to one or more other components of the laser tissue ablation system 100, so that the other component or components may take one or more actions in response to receiving the value of the determined spacing (Z).

In a second example, the processor circuitry 148 can cause the optical fiber 116 to retract proximally (e.g., by increasing the spacing (Z)), such as to avoid a flashing event that might damage the distal end 118 of the optical fiber 116. For example, the laser tissue ablation system 100 can further include an actuator 152 that can advance the optical fiber 116 distally and retract the optical fiber 116 proximally with respect to the endoscope 102. In some examples, such as the configuration of FIG. 1, the actuator 152 can include a wheel. The wheel can have a center that is fixed in position with respect to the endoscope 102. The wheel can have a circumferential surface that contacts the optical fiber 116. The wheel can be rotatable from a rotary actuator, such as a rotary actuator disposed at or near the center of the wheel. In some examples, the processor circuitry 148 can compare the determined spacing (Z) to a specified threshold, cause the actuator 152 to automatically reduce a difference between the determined spacing (Z) and the specified threshold. Such use of the threshold can effectively form a servo that can maintain the distal end 118 of the optical fiber 116 at a fixed distance away from the target 108.

In a third example, the processor circuitry 148 can vary at least one operational parameter of the therapeutic laser light source 114 in response to the determined spacing (Z), such as represented by the spacing data signal. For example, the processor circuitry 148 automatically switch off the therapeutic laser light source when the determined spacing (Z) represented by the spacing data signal is less than a specified threshold spacing. In other words, when the processor circuitry 148 has determined that the spacing (Z) is below a specified threshold, such as close enough to initiate a flashing event that could damage the distal end 118 of the optical fiber 116, the processor circuitry 148 can cause the therapeutic laser light source 114 to reduce an output power of the therapeutic laser light source 114, such as by automatically switching off the therapeutic laser light source 114. Decreasing the output power and/or turning off the therapeutic laser light source 114 can optionally be used in combination with another action, such as causing the actuator 152 to increase the determined spacing (Z).

In a fourth example, the video display 112, which can display the video image captured by the video camera 110 of the target 108 as illuminated by the illumination light source 104, can additionally display a visual representation of the determined spacing (Z) represented by the spacing data signal. In some examples, the visual representation can include one or more numerals that correspond to the determined spacing (Z) in suitable units, such as mm. In some examples, the visual representation can include one or more colors. For example, the video display 112 can display green when the determined spacing (Z) is within a specified range (e.g., a desired range for optimal operation of the laser tissue ablation system 100), yellow when the determined spacing (Z) is just outside the range, and red when the determined spacing (Z) is relatively far outside the range. Other color schemes can also be used. Other visual representations can also be used. In some examples, laser tissue ablation system 100 can optionally provide an audio alert that can alert the practitioner to the determined spacing (Z).

These are but four examples of actions taken in response to determining the spacing (Z) (e.g. the real-time separation) between the distal end 118 of the optical fiber 116 and the target 108. These actions can be executed singly or in any combination. Other actions can also be taken.

Figure 2:
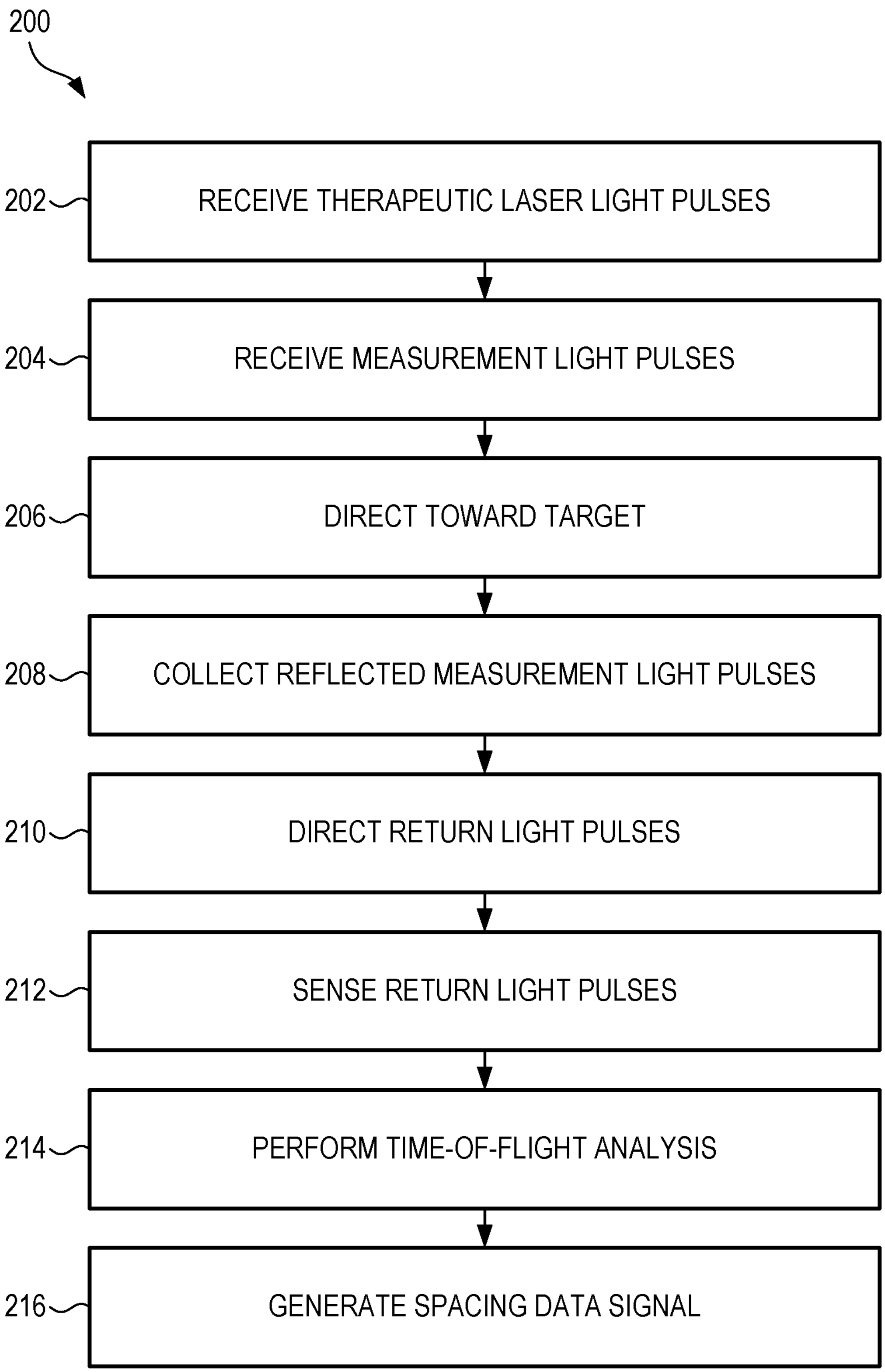
FIG. 2 shows a flow chart of an example of a method for operating a laser tissue ablation system.

FIG. 2 shows a flow chart of an example of a method 200 for operating a laser tissue ablation system, such as the laser tissue ablation system 100 of FIG. 1, or any other suitable laser tissue ablation system. The laser tissue ablation system can include an endoscope and an optical fiber including a distal end extending from the endoscope. The method 200 is but one example of a method for operating a laser tissue ablation system; other methods can also be used.

At operation 202, the optical fiber can receive therapeutic laser light pulses at first times.

At operation 204, the optical fiber can receive measurement light pulses at second times different from the first times.

At operation 206, the optical fiber can direct the therapeutic laser light pulses and the measurement light pulses along the optical fiber to emerge from the distal end of the optical fiber toward a target.

At operation 208, the optical fiber can collect, as collected light pulses, at least some of the measurement light pulses that are reflected from the target.

At operation 210, the optical fiber can direct, as return light pulses, at least some of the collected light pulses along the optical fiber away from the distal end of the optical fiber.

At operation 212, an optical detector can sense at least some of the return light pulses.

At operation 214, processor circuitry can perform a time-of-flight analysis of the sensed return light pulses to determine a spacing between the distal end of the optical fiber and the target.

At operation 216, the processor circuitry can generate a spacing data signal representing the determined spacing.

In some examples, performing the time-of-flight analysis can include, for an individual return light pulse, determining a time duration between the sensing of the return light pulse by the optical detector and an arrival of a corresponding reference signal.

In some examples, performing the time-of-flight analysis can include, for an individual return light pulse: determining a first amount of accumulated light for a first time duration of the return light pulse, determining a second amount of accumulated light for a second time duration of the return light pulse, and using a ratio of the first and second amounts of accumulated light to determine the spacing between the distal end of the optical fiber and the target.

In some examples, the method 200 can optionally further include: collecting, with the optical fiber, as collected therapeutic light pulses, at least some of the therapeutic light pulses that are reflected from the target; directing, as return therapeutic light pulses, at least some of the collected therapeutic light pulses along the optical fiber away from the distal end of the optical fiber; analyzing, with a spectrometer, the return therapeutic light pulses; and electronically communicating, to the spectrometer, data representing the determined spacing.

Figure 3:
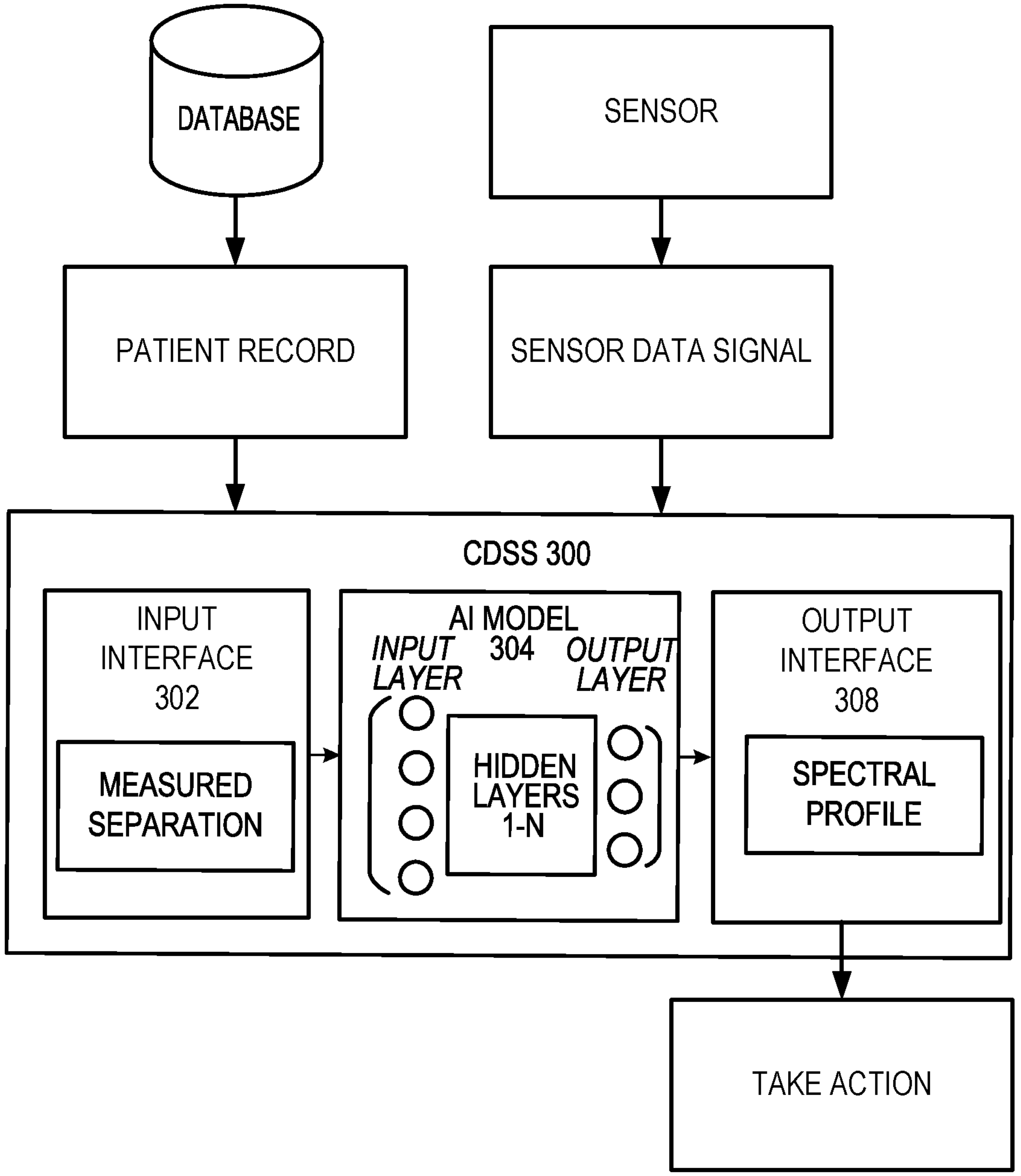
FIG. 3 shows a schematic diagram of an exemplary computer-based clinical decision support system that is configured to provide a value of distance.

FIG. 3 shows a schematic diagram of an exemplary computer-based clinical decision support system (CDSS) 300 that is configured to provide a value of distance (Z). For example, the optical property can include the optical power/intensity (I) of the return light. In various embodiments, the CDSS 300 includes an input interface 302 through which the optical property which is specific to a patient is provided as input features to an artificial intelligence (AI) model 304, a processor such as processor circuitry 148 which performs an inference operation in which the optical property is applied to the AI model to generate the value of distance (Z), and a user interface (UI) through which value of distance (Z) is communicated to a user, e.g., a clinician.

In some embodiments, the input interface 302 may be a direct data link between the CDSS 300 and one or more medical devices, such as laser tissue ablation system 100 or endoscope 102, which generate at least some of the input features. For example, the input interface 302 may transmit the optical property directly to the CDSS during a therapeutic and/or diagnostic medical procedure. Additionally, or alternatively, the input interface 302 may be a classical user interface that facilitates interaction between a user and the CDSS 300. For example, the input interface 302 may facilitate a user interface through which the user may manually enter the optical property. Additionally, or alternatively, the input interface 302 may provide the CDSS 300 with access to an electronic patient record from which one or more input features may be extracted. In any of these cases, the input interface 302 is configured to collect the optical property in association with a specific patient on or before a time at which the CDSS 300 is used to assess the medical condition addressed by the laser tissue ablation system 100 or endoscope 102, such as a kidney stone.

Based on one or more of the above input features, the processor such as processor circuitry 148 performs an inference operation using the AI model to generate the value of distance (Z). For example, input interface 302 may deliver the optical property into an input layer of the AI model which propagates this input feature through the AI model to an output layer. The AI model can provide a computer system the ability to perform tasks, without explicitly being programmed, by making inferences based on patterns found in the analysis of data. AI model explores the study and construction of algorithms (e.g., machine-learning algorithms) that may learn from existing data and make predictions about new data. Such algorithms operate by building an AI model from example training data in order to make data-driven predictions or decisions expressed as outputs or assessments.

There are two common modes for machine learning (ML): supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled and allowing the algorithm to act on that information without guidance. Unsupervised ML is useful in exploratory analysis because it can automatically identify structure in data.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model may be trained continuously or periodically prior to performance of the inference operation by the processor such as processor circuitry 148. Then, during the inference operation, the patient specific input features provided to the AI model may be propagated from an input layer, through one or more hidden layers, and ultimately to an output layer that corresponds to the value of distance (Z).

In some examples, the AI model can include a database, which can include data corresponding to a patient. The database can provide a patient record to the CDSS 300. IN some examples, the AI model can receive an optical property from a sensor, such as optical detector 140 or LIDAR detector 162.

During and/or subsequent to the inference operation, the value of distance (Z) may be communicated to the user via the user interface (UI) and/or automatically cause an actuator or an alarm connected to the processor to perform a desired action. For example, the processor can cause the actuator to move the optical fiber with respect to the endoscope. Alternatively, the processor can cause the alarm to alert the practitioner.

In some examples, the CDSS 300 can optionally be used to determine the action taken in response to a value of distance (Z).

Some features as described herein may provide methods and apparatus that can identify the composition of various targets, for instance, in medical applications (e.g., soft or hard tissue) in vivo through an endoscope. This may allow the operator to continuously monitor the composition of the target viewed through the endoscope throughout the procedure. This also can be used in combination with a laser system where the method may send feedback to the laser system to adjust the settings based on the composition of the target. This feature may allow for the instant adjustment of laser settings within a set range of the original laser setting selected by the operator.

Some features as described herein may be used to provide a system and method that measures differences, such as the chemical composition of a target, in vivo and suggests laser settings or automatically adjusts laser settings to better achieve a desired effect. Examples of targets and applications include laser lithotripsy of renal calculi and laser incision or vaporization of soft tissue. In one example, three major components are provided: the laser, the spectroscopy system, and the feedback analyzer. In an example, a controller of the laser system may automatically program laser therapy with appropriate laser parameter settings based on target composition. In an example, the laser may be controlled based on a machine learning algorithm trained with spectroscope data. Additionally or alternatively, an operator may receive an indication of target type continuously during the procedure, and be prompted to adjust the laser setting. By adjusting laser settings and adapting the laser therapy to composition portions of a single calculus target, stone ablation or dusting procedures can be performed faster and in a more energy-efficient manner.

Some features as described herein may provide systems and methods for providing data inputs to the feedback analyzer to include internet connectivity, and connectivity to other surgical devices with a measuring function. Additionally, the laser system may provide input data to another system such as an image processor whereby the procedure monitor may display information to the operator relevant to the medical procedure. One example of this is to identify different soft tissues more clearly in the field of view during a procedure, vasculature, capsular tissue, and different chemical compositions in the same target, such as a stone for example.

Some features as described herein may provide systems and methods for identifying different target types, such as different tissue types, or different calculus types. In some cases, a single calculus structure (e.g., a kidney, bladder, pancreobiliary, or gallbladder stone) may have two or more different compositions throughout its volume, such as brushite, calcium phosphate (CaP), dihydrate calcium oxalate (COD), monohydrate calcium oxalate (COM), magnesium ammonium phosphate (MAP), or a cholesterol-based or a uric acid-based calculus structure. For example, a target calculus structure may include a first portion of COD and a second portion of COM. According to one aspect, the present document describes a system and a method for continuously identifying different compositions contained in a single target (e.g., a single stone) based on continuous collection and analysis of spectroscopic data in vivo. The treatment (e.g., laser therapy) may be adapted in accordance with the identified target composition. For example, in response to an identification of a first composition (e.g., COD) in a target stone, the laser system may be programmed with a first laser parameter setting (e.g., power, exposure time, or firing angle, etc.) and deliver laser beams accordingly to ablate or dust the first portion. Spectroscopic data may be continuously collected and analyzed during the laser therapy. In response to an identification of a second composition (e.g., COM) different than the first composition in the same target stone being treated, the laser therapy may be adjusted such as by programing the laser system with a second laser parameter setting different from the laser parameter setting (e.g., different power, or exposure time, or firing angle, etc.), and delivering laser beams accordingly to ablate or dust the second portion of the same target stone. In some examples, multiple different laser sources may be included in the laser system. Stone portions of different compositions may be treated by different laser sources. The appropriate laser to use may be determined by the identification of stone type.

Some features as described herein may be used in relation to a laser system for various applications where it may be advantageous to incorporate different types of laser sources. For instance, the features described herein may be suitable in industrial or medical settings, such as medical diagnostic, therapeutic and surgical procedures. Features as described herein may be used regarding an endoscope, laser surgery, laser lithotripsy, laser settings, and/or spectroscopy.

In the foregoing detailed description, the method and apparatus of the present disclosure have been described with reference to specific embodiments thereof. It will, however, be evident that various modifications and changes may be made thereto without departing from the broader spirit and scope of the present disclosure. The present specification and figures are accordingly to be regarded as illustrative rather than restrictive.

To further illustrate the device and related method disclosed herein, a non-limiting list of examples is provided below. Each of the following non limiting examples can stand on its own or can be combined in any permutation or combination with any one or more of the other examples.

In Example 1, a laser tissue ablation system can comprise: an endoscope; an optical fiber including a distal end extending from the endoscope, the optical fiber configured to: receive therapeutic laser light pulses at first times; receive measurement light pulses at second times different from the first times; direct the therapeutic laser light pulses and the measurement light pulses along the optical fiber to emerge from the distal end of the optical fiber toward a target; collect, as collected light pulses, at least some of the measurement light pulses that are reflected from the target; and direct, as return light pulses, at least some of the collected light pulses along the optical fiber away from the distal end of the optical fiber; an optical detector configured to sense at least some of the return light pulses; and processor circuitry configured to: perform a time-of-flight analysis of the sensed return light pulses to determine a spacing between the distal end of the optical fiber and the target; and generate a spacing data signal representing the determined spacing.

In Example 2, the laser tissue ablation system of Example 1 can optionally further comprise: a therapeutic laser light source spaced apart from the endoscope and configured to generate the therapeutic laser light pulses at the first times; and a measurement light source spaced apart from the endoscope and configured to generate the measurement light pulses at the second times.

In Example 3, the laser tissue ablation system of any one of Examples 1-2 can optionally be configured such that the processor circuitry is configured to perform the time-of-flight analysis of the sensed return light pulses by, for an individual return light pulse, determining a time duration between the sensing of the return light pulse by the optical detector and an arrival of a corresponding reference signal.

In Example 4, the laser tissue ablation system of any one of Examples 1-3 can optionally be configured such that: the measurement light pulses reflect from the distal end of the optical fiber to form reference light pulses that propagate along the optical fiber away from the distal end of the optical fiber; and the optical detector is further configured to sense at least some of the reference light pulses, and, in response, form the reference signals.

In Example 5, the laser tissue ablation system of any one of Examples 1-4 can optionally be configured such that the measurement light source is further configured to generate reference electrical pulses at times that correspond to the measurement light pulses, the reference electrical pulses forming the reference signals.

In Example 6, the laser tissue ablation system of any one of Examples 1-5 can optionally be configured such that: the measurement light source includes a first light source configured to generate first measurement light pulses at a first wavelength and a second light source configured to generate second measurement light pulses at a second wavelength different from the first wavelength; the optical fiber includes a fiber material having non-zero dispersion such that the first measurement light pulses and the second measurement light pulses propagate along the optical fiber at different speeds; the first measurement light pulses form the return light pulses; and the second measurement light pulses are sensed by the optical detector to form the corresponding reference signals.

In Example 7, the laser tissue ablation system of any one of Examples 1-6 can optionally be configured such that the processor circuitry is configured to perform the time-of-flight analysis of the sensed return light pulses by, for an individual return light pulse: determining a first amount of accumulated light for a first time duration of the return light pulse; determining a second amount of accumulated light for a second time duration of the return light pulse; and using a ratio of the first and second amounts of accumulated light to determine the spacing between the distal end of the optical fiber and the target.

In Example 8, the laser tissue ablation system of any one of Examples 1-7 can optionally further comprise: an actuator configured to advance the optical fiber distally and retract the optical fiber proximally with respect to the endoscope, wherein the processor circuitry is further configured to: compare the determined spacing to a specified threshold; and cause the actuator to automatically reduce a difference between the determined spacing and the specified threshold.

In Example 9, the laser tissue ablation system of any one of Examples 1-8 can optionally be configured such that: the actuator comprises a wheel; the wheel has a center that is fixed in position with respect to the endoscope; the wheel has a circumferential surface that contacts the optical fiber; and the wheel is rotatable from a rotary actuator.

In Example 10, the laser tissue ablation system of any one of Examples 1-9 can optionally be configured such that the processor circuitry is further configured to vary at least one operational parameter of the therapeutic laser light source in response to the determined spacing represented by the spacing data signal.

In Example 11, the laser tissue ablation system of any one of Examples 1-10 can optionally be configured such that the processor circuitry is further configured to automatically switch off the therapeutic laser light source when the determined spacing represented by the spacing data signal is less than a specified threshold spacing.

In Example 12, the laser tissue ablation system of any one of Examples 1-11 can optionally further comprise: an illumination light source disposed at a distal end of the endoscope and configured to illuminate the target with visible illumination light; a camera disposed at the distal end of the endoscope and configured to generate a video image of the illuminated target; and a display coupled to the processor circuitry and configured to display the video image of the illuminated target and a visual representation of the determined spacing represented by the spacing data signal.

In Example 13, the laser tissue ablation system of any one of Examples 1-12 can optionally be configured such that: the therapeutic laser light source is configured to direct the therapeutic laser light pulses along a first optical path; the measurement light source is configured to direct the measurement light pulses along a second optical path, the measurement light pulses being spectrally separated from the therapeutic laser light pulses; and the laser tissue ablation system further comprises a dichroic beamsplitter positioned to combine the first and second optical paths to align along a third optical path that extends into the optical fiber.

In Example 14, the laser tissue ablation system of any one of Examples 1-13 can optionally be configured such that: the optical fiber is further configured to: collect, as collected therapeutic light pulses, at least some of the therapeutic light pulses that are reflected from the target; and direct, as return therapeutic light pulses, at least some of the collected therapeutic light pulses along the optical fiber away from the distal end of the optical fiber; and the laser tissue ablation system further comprises a spectrometer configured to analyze the return therapeutic light pulses.

In Example 15, the laser tissue ablation system of any one of Examples 1-14 can optionally be configured such that: the measurement light source is a LIDAR light source; the optical detector is a LIDAR detector; and the laser tissue ablation system further comprises a beamsplitter configured to: separate the return light pulses from the return therapeutic light pulses; direct the return light pulses to the LIDAR detector; and direct the return therapeutic light pulses to the spectrometer; and the processor circuitry is configured to electronically communicate to the spectrometer data representing the determined spacing.

In Example 16, a method for operating a laser tissue ablation system that includes an endoscope and an optical fiber including a distal end extending from the endoscope can comprise: receiving, with the optical fiber, therapeutic laser light pulses at first times; receiving, with the optical fiber, measurement light pulses at second times different from the first times; directing the therapeutic laser light pulses and the measurement light pulses along the optical fiber to emerge from the distal end of the optical fiber toward a target; collecting, with the optical fiber, as collected light pulses, at least some of the measurement light pulses that are reflected from the target; directing, as return light pulses, at least some of the collected light pulses along the optical fiber away from the distal end of the optical fiber; sensing, with an optical detector, at least some of the return light pulses; performing a time-of-flight analysis of the sensed return light pulses to determine a spacing between the distal end of the optical fiber and the target; and generating a spacing data signal representing the determined spacing.

In Example 17, the method of Example 16 can optionally be configured such that performing the time-of-flight analysis comprises, for an individual return light pulse: determining a time duration between the sensing of the return light pulse by the optical detector and an arrival of a corresponding reference signal.

In Example 18, the method of any one of Examples 16-17 can optionally be configured such that performing the time-of-flight analysis comprises, for an individual return light pulse: determining a first amount of accumulated light for a first time duration of the return light pulse; determining a second amount of accumulated light for a second time duration of the return light pulse; and using a ratio of the first and second amounts of accumulated light to determine the spacing between the distal end of the optical fiber and the target.

In Example 19, the method of any one of Examples 16-18 can optionally further comprise: collecting, with the optical fiber, as collected therapeutic light pulses, at least some of the therapeutic light pulses that are reflected from the target; directing, as return therapeutic light pulses, at least some of the collected therapeutic light pulses along the optical fiber away from the distal end of the optical fiber; analyzing, with a spectrometer, the return therapeutic light pulses; and electronically communicating, to the spectrometer, data representing the determined spacing.

In Example 20, a laser tissue ablation system can comprise: a therapeutic laser light source configured to generate therapeutic laser light pulses at first times; a measurement light source configured to generate measurement light pulses at second times different from the first times; an endoscope spaced apart from the therapeutic laser light source and the measurement light source; an optical fiber including a distal end extending from the endoscope and configured to: direct the therapeutic laser light pulses and the measurement light pulses along the optical fiber to emerge from the distal end of the optical fiber toward a target; collect, as collected light pulses, at least some of the measurement light pulses that are reflected from the target; direct, as return light pulses, at least some of the collected light pulses along the optical fiber away from the distal end of the optical fiber; collect, as collected therapeutic light pulses, at least some of the therapeutic light pulses that are reflected from the target; and direct, as return therapeutic light pulses, at least some of the collected therapeutic light pulses along the optical fiber away from the distal end of the optical fiber; an optical detector configured to sense at least some of the return light pulses; a spectrometer configured to analyze the return therapeutic light pulses; processor circuitry configured to: perform a time-of-flight analysis of the sensed return light pulses to determine a spacing between the distal end of the optical fiber and the target; generate a spacing data signal representing the determined spacing; and electronically communicate the spacing data signal to the spectrometer; an illumination light source disposed at a distal end of the endoscope and configured to illuminate the target with visible illumination light; a camera disposed at the distal end of the endoscope and configured to generate a video image of the illuminated target; and a display coupled to the processor circuitry and configured to display the video image of the illuminated target and a visual representation of the determined spacing represented by the spacing data signal.

What is claimed is:

1. A laser tissue ablation system, comprising:

an endoscope;

a therapeutic laser light source spaced apart from the endoscope and configured to generate therapeutic laser light pulses at first times;

a measurement light source spaced apart from the endoscope and configured to generate measurement light pulses at second times different from the first times;

an optical fiber including a distal end extending from the endoscope, the optical fiber configured to:

receive the therapeutic laser light pulses at the first times;

receive the measurement light pulses at the second times;

direct the therapeutic laser light pulses and the measurement light pulses along the optical fiber to emerge from the distal end of the optical fiber toward a target;

collect, as collected light pulses, at least some of the measurement light pulses that are reflected from the target; and direct, as return light pulses, at least some of the collected light pulses along the optical fiber away from the distal end of the optical fiber;

an optical detector configured to sense at least some of the return light pulses; and processor circuitry configured to:

perform a time-of-flight analysis of the sensed return light pulses to determine a spacing between the distal end of the optical fiber and the target by, for an individual return light pulse, determining a time duration between the sensing of the return light pulse by the optical detector and an arrival at the processor circuitry of a corresponding reference signal; and generate a spacing data signal representing the determined spacing;

wherein:

the measurement light pulses reflect from the distal end of the optical fiber to form reference light pulses that propagate along the optical fiber away from the distal end of the optical fiber; and the optical detector is further configured to sense at least some of the reference light pulses, and, in response, form the reference signals.

2. The laser tissue ablation system of claim 1, wherein the measurement light source is further configured to generate reference electrical pulses at times that correspond to the measurement light pulses, the reference electrical pulses forming the reference signals.

3. The laser tissue ablation system of claim 1, wherein the processor circuitry is further configured to vary at least one operational parameter of the therapeutic laser light source in response to the determined spacing represented by the spacing data signal.

4. The laser tissue ablation system of claim 1, wherein:

the therapeutic laser light source is configured to direct the therapeutic laser light pulses along a first optical path;

the measurement light source is configured to direct the measurement light pulses along a second optical path, the measurement light pulses being spectrally separated from the therapeutic laser light pulses; and the laser tissue ablation system further comprises a dichroic beamsplitter positioned to combine the first and second optical paths to align along a third optical path that extends into the optical fiber.

5. The laser tissue ablation system of claim 1, wherein the processor circuitry is further configured to automatically switch off the therapeutic laser light source when the determined spacing represented by the spacing data signal is less than a specified threshold spacing.

6. The laser tissue ablation system of claim 1, wherein:

the optical fiber is further configured to:

collect, as collected therapeutic light pulses, at least some of the therapeutic light pulses that are reflected from the target;

direct, as return therapeutic light pulses, at least some of the collected therapeutic light pulses along the optical fiber away from the distal end of the optical fiber; and the laser tissue ablation system further comprises a spectrometer configured to analyze the return therapeutic light pulses.

7. The laser tissue ablation system of claim 6, wherein:

the measurement light source is a LIDAR light source;

the optical detector is a LIDAR detector;

the laser tissue ablation system further comprises a beamsplitter configured to:

separate the return light pulses from the return therapeutic light pulses;

direct the return light pulses to the LIDAR detector; and direct the return therapeutic light pulses to the spectrometer; and the processor circuitry is configured to electronically communicate, to the spectrometer, data representing the determined spacing.

8. The laser tissue ablation system of claim 1, further comprising:

an actuator configured to advance the optical fiber distally and retract the optical fiber proximally with respect to the endoscope, wherein the processor circuitry is further configured to:

compare the determined spacing to a specified threshold; and cause the actuator to automatically reduce a difference between the determined spacing and the specified threshold.

9. The laser tissue ablation system of claim 8, wherein:

the actuator comprises a wheel;

the wheel has a center that is fixed in position with respect to the endoscope;

the wheel has a circumferential surface that contacts the optical fiber; and the wheel is rotatable from a rotary actuator.

10. The laser tissue ablation system of claim 1, further comprising:

an illumination light source disposed at a distal end of the endoscope and configured to illuminate the target with visible illumination light;

a camera disposed at the distal end of the endoscope and configured to generate a video image of the illuminated target; and a display coupled to the processor circuitry and configured to display the video image of the illuminated target and a visual representation of the determined spacing represented by the spacing data signal.

11. A laser tissue ablation system, comprising:

an endoscope;

a therapeutic laser light source spaced apart from the endoscope and configured to generate therapeutic laser light pulses at first times;

a measurement light source spaced apart from the endoscope and configured to generate measurement light pulses at second times different from the first times;

an optical fiber including a distal end extending from the endoscope, the optical fiber configured to:

receive the therapeutic laser light pulses at the first times;

receive the measurement light pulses at the second times;

direct the therapeutic laser light pulses and the measurement light pulses along the optical fiber to emerge from the distal end of the optical fiber toward a target;

collect, as collected light pulses, at least some of the measurement light pulses that are reflected from the target; and direct, as return light pulses, at least some of the collected light pulses along the optical fiber away from the distal end of the optical fiber;

an optical detector configured to sense at least some of the return light pulses; and processor circuitry configured to:

perform a time-of-flight analysis of the sensed return light pulses to determine a spacing between the distal end of the optical fiber and the target by, for an individual return light pulse, determining a time duration between the sensing of the return light pulse by the optical detector and an arrival at the processor circuitry of a corresponding reference signal; and generate a spacing data signal representing the determined spacing;

wherein:

the measurement light source includes a first light source configured to generate first measurement light pulses at a first wavelength and a second light source configured to generate second measurement light pulses at a second wavelength different from the first wavelength;

the optical fiber includes a fiber material having non-zero dispersion such that the first measurement light pulses and the second measurement light pulses propagate along the optical fiber at different speeds;

the first measurement light pulses form the return light pulses; and the second measurement light pulses are sensed by the optical detector to form the corresponding reference signals.

12. The laser tissue ablation system of claim 11, wherein the measurement light source is further configured to generate reference electrical pulses at times that correspond to the measurement light pulses, the reference electrical pulses forming the reference signals.

13. The laser tissue ablation system of claim 11, wherein the processor circuitry is further configured to vary at least one operational parameter of the therapeutic laser light source in response to the determined spacing represented by the spacing data signal.

14. The laser tissue ablation system of claim 11, wherein:

the therapeutic laser light source is configured to direct the therapeutic laser light pulses along a first optical path;

the measurement light source is configured to direct the measurement light pulses along a second optical path, the measurement light pulses being spectrally separated from the therapeutic laser light pulses; and the laser tissue ablation system further comprises a dichroic beamsplitter positioned to combine the first and second optical paths to align along a third optical path that extends into the optical fiber.

15. The laser tissue ablation system of claim 11, wherein the processor circuitry is further configured to automatically switch off the therapeutic laser light source when the determined spacing represented by the spacing data signal is less than a specified threshold spacing.

16. The laser tissue ablation system of claim 11, wherein the optical fiber is further configured to:

collect, as collected therapeutic light pulses, at least some of the therapeutic light pulses that are reflected from the target;

direct, as return therapeutic light pulses, at least some of the collected therapeutic light pulses along the optical fiber away from the distal end of the optical fiber; and the laser tissue ablation system further comprises a spectrometer configured to analyze the return therapeutic light pulses.

17. The laser tissue ablation system of claim 16, wherein:

the measurement light source is a LIDAR light source;

the optical detector is a LIDAR detector;

the laser tissue ablation system further comprises a beam-splitter configured to:

separate the return light pulses from the return therapeutic light pulses;

direct the return light pulses to the LIDAR detector; and direct the return therapeutic light pulses to the spectrometer; and the processor circuitry is configured to electronically communicate, to the spectrometer, data representing the determined spacing.

18. The laser tissue ablation system of claim 11, further comprising:

an actuator configured to advance the optical fiber distally and retract the optical fiber proximally with respect to the endoscope, wherein the processor circuitry is further configured to:

compare the determined spacing to a specified threshold; and cause the actuator to automatically reduce a difference between the determined spacing and the specified threshold.

19. The laser tissue ablation system of claim 18, wherein:

the actuator comprises a wheel;

the wheel has a center that is fixed in position with respect to the endoscope;

the wheel has a circumferential surface that contacts the optical fiber; and the wheel is rotatable from a rotary actuator.

20. The laser tissue ablation system of claim 1, further comprising:

an illumination light source disposed at a distal end of the endoscope and configured to illuminate the target with visible illumination light;

a camera disposed at the distal end of the endoscope and configured to generate a video image of the illuminated target; and a display coupled to the processor circuitry and configured to display the video image of the illuminated target and a visual representation of the determined spacing represented by the spacing data signal.

* * * * *